United States Patent [19]

DeColibus et al.

[11] Patent Number: 4,529,816
[45] Date of Patent: Jul. 16, 1985

[54] PROCESS FOR PRODUCING ALKYL METHACRYLATES

[75] Inventors: Raymond L. DeColibus, Bartlett; Jan J. van Heiningen; Thomas F. Veerkamp, both of Memphis, all of Tenn.

[73] Assignee: E. I. Du Pont De Nemours and Company, Wilmington, Del.

[21] Appl. No.: 579,567

[22] Filed: Feb. 13, 1984

[51] Int. Cl.$^3$ .................... C07C 67/327; C07C 67/20
[52] U.S. Cl. ................................... 560/212; 560/215
[58] Field of Search ............................. 560/215, 212

[56] References Cited

U.S. PATENT DOCUMENTS

| 2,041,820 | 5/1936 | Crawford | 560/212 |
| 2,101,821 | 12/1937 | Crawford | 560/215 |
| 2,811,545 | 10/1957 | Steadman | 560/212 |
| 3,974,207 | 8/1976 | Szelejewski et al. | 560/212 |

Primary Examiner—Natalie Trousof
Assistant Examiner—L. Hendriksen

[57] ABSTRACT

In the process for making alkyl methacrylates from acetone cyanohydrin and $H_2SO_4$, it has been found that alkyl 2-hydroxy-2-methyl propionate made during the process can be collected and returned to the process sequence just prior to the esterification step where it can be dehydrated to alkyl methacrylate.

3 Claims, No Drawings

PROCESS FOR PRODUCING ALKYL METHACRYLATES

FIELD OF THE INVENTION

This invention relates to an improvement in a process for making alkyl methacrylates.

BACKGROUND OF THE INVENTION

Methyl methacrylate (MMA), which is representative of alkyl methacrylates, can be prepared in a reaction sequence starting with acetone cyanohydrin. In this process acetone cyanohydrin (ACN) is treated with sulfuric acid to form 2-hydroxy-2-methylpropionamide (HiBAm) and its sulfate ester (HiBAm.SE). These two compounds are then subjected to heat to form methacrylamide (MAAm). The MAAm is then treated with methyl alcohol and water to form methyl methacrylate (MMA). This reaction sequence is depicted as follows:

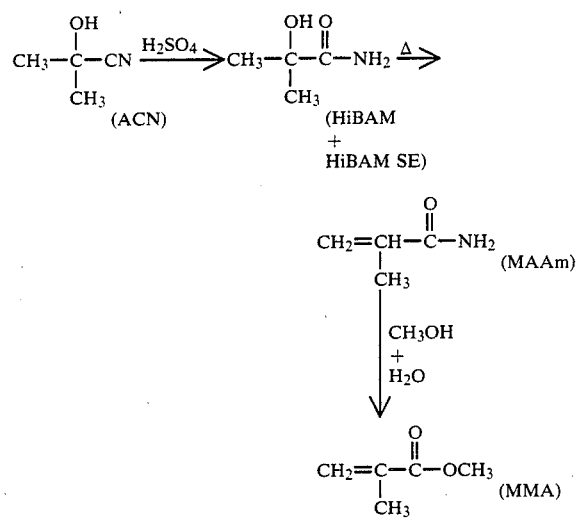

Because HiBAm reacts more slowly than HiBAm.SE to form MAAm the reaction time in the heat step must be extended and/or the temperature raised to reduce unreacted HiBAm. But there are limits to extending these parameters and not all the HiBAm is reacted, thus HiBAm is present when the MAAm is treated with CH$_3$OH and H$_2$O. The HiBAm present also reacts with the CH$_3$OH and H$_2$O, to form methyl 2-hydroxy-2-methyl propionate (MHiB). This reaction is depicted as follows:

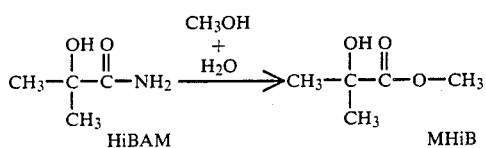

The presence of the HiBAm reduces yield of MMA for several reasons. First, it is material that could have been converted to MAAm but wasn't; thus, less MAAm is present for conversion to MMA. Second, as HiBAm is heated longer or at a higher temperature to increase yield of MAAm, the heat begins to decompose the MAAm; thus reducing the amount of MAAm available for conversion to MMA.

It would be advantageous to find some means of preventing or reducing yield loss caused by presence of the HiBAm in the esterification step.

SUMMARY OF THE INVENTION

In the process for preparing alkyl methacrylates by
(1) reacting acetone cyanohydrin (ACN) with sulfuric acid to form

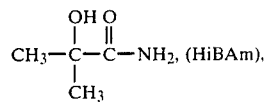

(2) dehydrating the HiBAm by heating at between 90°–160° C. to form methacrylamide (MAAm) which contains some unreacted HiBAm,
(3) esterifying with a C$_1$–C$_{10}$ alkyl alcohol whereby the MAAm forms alkyl methacrylate and the residual HiBAm forms

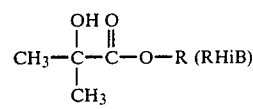

where R is lower alkyl, and
(4) concentrating the RHiB, the improvement wherein
(a) The RHiB from step (4) is collected and then
(b) the RHiB is returned to the process sequence intermediate steps (2) and (3) whereby H$_2$SO$_4$ already present and heat from step (2) is sufficient to dehydrate the RHiB to form alkyl methacrylate.

In another aspect of this invention, the RHiB added intermediate steps (2) and (3) need not be the RHiB concentrated in step (4). On the contrary it can be RHiB obtained from another independent source.

DESCRIPTION OF THE INVENTION

The improvement of this invention is based on the discovery that residual alkyl-2-hydroxy-2-methyl propionate (RHiB) in the alkyl methacrylate product can be collected and returned to the process sequence where the amount of H$_2$SO$_4$ already present and the heat already in the system intermediate steps (2) and (3) is sufficient to directly dehydrate the RHiB to alkyl methacrylate.

The dehydration reaction is represented by the equation:

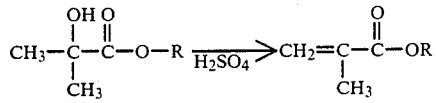

By returning the RHiB to the process sequence, a major yield increase is obtained. By being able to collect and return the RHiB, it is not necessary to extend the time and/or raise the temperature in the HiBAm dehydration step described further above. Thus, decomposition of the MAAm formed is reduced.

To return RHiB to the process sequence, the RHiB formed along with alkyl methacrylate in the esterification step is concentrated in a distillation stream subsequent to the esterification step. The RHiB so concentrated is then added to the stream of MAAm produced in the main process before the stream enters the esterification zone. The stream of MAAm contains residual H$_2$SO$_4$ which surprisingly is present in an amount strong enough to substantially dehydrate the RHiB to alkyl methacrylate before the esterification step begins.

When RHiB is added to the MAAm stream, the strength of the H$_2$SO$_4$ in the stream should be about 97–100%, preferably 100%, the mole ratio of the free H$_2$SO$_4$ to RHiB should be maintained between 4 and 40, preferably 7–15. The residence time between addition of the RHiB and entry into the esterification zone (as measured at the point of entry of the alkyl alcohol) is not critical, but preferably is between 4 and 60 seconds, depending on the temperature, which generally is between 100° and 150° C. However higher and lower temperatures may be used. The amount of water in the amide stream should be low, e.g., less than 3% because presence of water retards the dehydration of RHiB. If the H$_2$SO$_4$ concentration is too low, more can be added along with the RHiB.

A beneficial aspect is that neither the recycled RHiB nor the sulfuric acid required for its dehydration need be totally isolated from the other stream components presently found in a conventional acetone cyanohydrin type alkyl methacrylate production facility. Further, the sulfuric acid present is essentially present free of cost since it is already present from the earlier AC-N—H$_2$SO$_4$ reaction step.

It is also of benefit to control residence time distribution while mixing the RHiB with the amide/H$_2$SO$_4$ mix. The distribution of residence time should be as narrow as possible; approaching pure plug flow. This can be achieved by employing a static mixer intermediate steps (2) and (3). The mixer then serves as a dehydrator in which the RHiB is dehydrated to form alkyl methacrylate.

The reaction sequence in making alkyl methacrylates from acetone cyanohydrin and sulfuric acid is well known. Acetone cyanohydrin is treated with sulfuric acid which contains sufficient SO$_3$ to provide an acid strength of at least 98%, preferably at least 99.5%, to produce a mixture containing methacrylamide. Preferably the sulfuric acid is employed in the form of fuming sulfuric acid (which is also called oleum). The amount of such sulfuric acid employed is preferably an amount which provides a weight ratio to the acetone cyanohydrin of between about 1.3 and 1.8. Preferably the two ingredients are mixed at a temperature below 110° C. and then subjected to a temperature in the range of 130°–150° C. for a time sufficient to obtain optimum yield of methacrylamide (as determined by withdrawal of samples at regular intervals and analysis of the samples). Ordinarily, a polymerization inhibitor, such as copper sulfate, is employed. If desired the acetone cyanohydrin can be added in two or more portions. In this embodiment the first portion (50–60% of the total cyanohydrin) is added below 110° C. and held at that temperature for about 10 to 20 minutes at which time the remainder of the cyanohydrin is added, also preferably below 110° C. For a single addition of the acetone cyanohydrin the strength of the sulfuric acid is preferably between 99–101%; when the acetone cyanohydrin is added for the two-stage addition the acid strength is preferably between about 98–100%.

The mixture is then treated with an excess of water and an alkyl alcohol (preferably of 1–6 carbon atoms) at about 100° to 150° C. to obtain an alkyl ester of methacrylic acid.

EXAMPLES

Example 1

In this Example, methacrylamide (MAAm), prepared from the reaction of acetone cyanohydrin and sulfuric acid followed by heating at 133° C. was obtained from a commercial process stream. The stream contained
63.0% H$_2$SO$_4$
32.1% MAAm
0.37% MAA
1.33% HiBAm The collected stream was kept at 90°–100° C. to prevent salting out until it was ready to be passed through a "Kenics" static mixer used as a plug-flow dehydrator. The stream was injected into the dehydrator at a flow rate of 31.35 g/min, and a commercially obtained sample of MHiB at a flow-rate of 0.656 g/min was also injected (0.168 mmole/g).

Hold up time in the hydrator was 9.9 seconds and the temperature was held between 129 and 134° C.

Yield of MMA and MAA (minus the MAA level in the original stream) was 0.107 mmole/g or 63.7% yield. Unreacted MHiB still present was 0.53 mmole/g or 31.5% unreacted MHiB.

Recovery determined by the formula $$\text{Recovery} = \frac{\text{MMA} + (\text{MAA} - \text{MMA}_o) + \text{MHiB}}{\text{MHiB}_o}$$

was 95%, indicating low yield loss.

This Example demonstrates that MHiB will dehydrate to MMA when inserted into a stream of MAAm obtained from reaction of ACN and H$_2$SO$_4$.

Example 2

In this Example, the process stream was collected as in Example 1. It contained
62.3% H$_2$SO$_4$
37.4% MAAm and
small amounts of MAA and HiBAm The stream sample was passed through the same dehydrator at a rate of 17.88 g/min along with butyl 2-hydroxy-2-methylpropionate (BHiB) at a rate of 0.42 g/min (0.115 mmole/g). Hold up time in the dehydrator was 17.6 seconds and the temperature in the dehydrator was between 129° and 138° C. Yield of BHiB to butyl methacrylate was 32%.

This Example shows that higher-alkyl methacrylate can be obtained.

Example 3

In this Example the MHiB used was obtained from the distillation column designed to remove high boilers (tails) of a commercial acetone cyanohydrin preparation of MMA.

As with Examples 1 and 2, a process stream was collected. It contained
61.4% H$_2$SO$_4$
35.1% MAAm and
minor amounts of MAA and HiBAm The stream was passed through the same dehydrator used in Examples 1 and 2 at a flow rate of 17.02 g/min. Tails from the distillation column used in the preparation of MMA were collected and analysed as:
44.4% MMA
37.6% MAA 8.01% MHiB
3.1% H₂O The tails were passed through the dehydrator at a rate of 3.89 g/min. (0.126 mmole/g or 14900 ppm MHiB). Hold up time in the dehydrator was 5.8 seconds and the temperature was 137°–140° C. The MHiB remaining after dehydration was 6835 ppm or 45.9% unreacted MHiB.

This Example demonstrates that MHiB present in a product stream can be recycled and dehydrated in a product stream of MAAm.

We claim:

1. In the process for preparing alkyl methacrylates by
   (1) reacting acetone cyanohydrin (ACN) with sulfuric acid to form

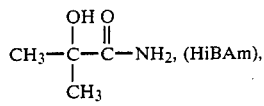

(2) dehydrating the HiBam by heating at between 90°–160° C. to form methacrylamide (MAAm) which contains some unreacted HiBAm,
   (3) esterifying with a $C_1$–$C_{10}$ alkyl alcohol whereby the MAAm forms alkyl methacrylate and the residual HiBAm forms

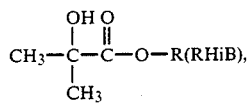

and
   (4) concentrating the RHiB, the improvements wherein
   (a) The RHiB from step (4) is collected and then
   (b) the RHiB is returned to the process sequence intermediate steps (2) and (3) whereby $H_2SO_4$ already present and heat from step (2) is sufficient to dehydrate the RHiB to form alkyl methacrylate,
   (c) in the stream intermediate steps (2) and (3), the strength of the $H_2SO_4$ is between 97–100%, the mole ratio of free $H_2SO_4$ to RHiB is between 4 and 40, and the temperature of the stream is between about 100° and 150° C.

2. The process of claim 1 wherein the $C_1$–$C_{10}$ alkyl alcohol used in step (3) is methyl alcohol.

3. In the process for preparing alkyl methacrylates by
   (1) reacting acetone cyanohydrin (ACN) with sulfuric acid to form

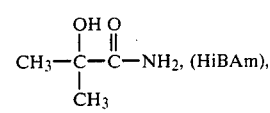

(2) dehydrating the HiBAm by heating at between 90°–160° C. to form methacrylamide (MAAm) which contains some unreacted HiBAm,
   (3) esterifying with a $C_1$–$C_{10}$ alkyl alcohol whereby the MAAm forms alkyl methacrylate and the residual HiBAm forms

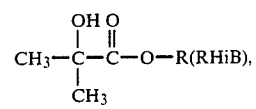

the improvemnts comprising adding RHiB intermediate steps (2) and (3) whereby $H_2SO_4$ already present and heat from step (2) is sufficient to dehydrate the RHiB, and in the stream intermediate steps (2) and (3), the strength of the $H_2SO_4$ is between 97–100%, the mole ratio of free $H_2SO_4$ to RHiB is between 4 and 40, and the temperature of the stream is between about 100° and 150° C.

* * * * *